US00PP28844P3

(12) United States Plant Patent
Beekenkamp

(10) Patent No.: US PP28,844 P3
(45) Date of Patent: Jan. 2, 2018

(54) ***DAHLIA* PLANT NAMED 'BKDAOBI'**

(50) Latin Name: *Dahlia hybrida*
Varietal Denomination: BKDAOBI

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 31 days.

(21) Appl. No.: 14/999,401

(22) Filed: May 3, 2016

(65) Prior Publication Data

US 2017/0325379 P1 Nov. 9, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Keith Robinson
(74) *Attorney, Agent, or Firm* — C. A. Whealy

(57) ABSTRACT

A new and distinct cultivar of *Dahlia* plant named 'BKDAOBI', characterized by its broadly upright plant habit; freely basal branching habit; dense and bushy growth habit; medium-sized dark green-colored leaves; and large decorative inflorescences with orange and red bi-colored ray florets.

2 Drawing Sheets

Botanical designation: *Dahlia hybrida.*
Cultivar denomination: 'BKDAOBI'.

BACKGROUND OF THE INVENTION

The present invention relates to a new and distinct cultivar of *Dahlia* plant, botanically known as *Dahlia hybrida* and hereinafter referred to by the name 'BKDAOBI'.

The new *Dahlia* plant is a product of a planned breeding program conducted by the Inventor in Maasdijk, The Netherlands. The objective of the breeding program is to create new container *Dahlia* plants that have a freely basal branching habit, and large decorative inflorescences with attractive ray floret coloration.

The new *Dahlia* plant is a naturally-occurring branch mutation of *Dahlia hybrida* 'BKDADO', disclosed in U.S. Plant Pat. No. 28,287. The new *Dahlia* plant was discovered and selected by the Inventor on a single flowering plant from within a population of plants of 'BKDADO' in a controlled greenhouse environment in Maasdijk, The Netherlands in April, 2013.

Asexual reproduction of the new *Dahlia* plant by terminal cuttings in a controlled greenhouse environment in Maasdijk, The Netherlands since June, 2013 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAOBI'. These characteristics in combination distinguish 'BKDAOBI' as a new and distinct *Dahlia* plant:

1. Broadly upright plant habit.
2. Freely basal branching habit; dense and bushy growth habit.
3. Medium-sized dark green-colored leaves.
4. Large decorative inflorescences with orange and red bi-colored ray florets.

Plants of the new *Dahlia* differ primarily from plants of the mutation parent, 'BKDADO', in ray floret color as plants of 'BKDADO' have solid orange-colored ray florets.

Plants of the new *Dahlia* can be compared to plants of *Dahlia hybrida* 'BKDAOR', disclosed in U.S. Plant Pat. No. 23,487. In side-by-side comparisons, plants of the new *Dahlia* differ from plants of 'BKDAOR' in the following characteristics:

1. Plants of the new *Dahlia* have lighter green-colored leaves than plants of 'BKDAOR'.
2. Plants of the new *Dahlia* and 'BKDAOR' differ in ray floret color as plants of 'BKDAOR' have yellow to yellow orange-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'BKDAOBI' grown in a container.

The photograph on the second sheet is a close-up view of a typical inflorescence of 'BKDAOBI'.

DETAILED BOTANICAL DESCRIPTION

The aforementioned photographs and the following observations and measurements describe plants grown during the winter in 15-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were nine weeks old when the photographs and description were taken. To induce inflorescence initiation and development, plants were grown under short nyctoperiod (long day) conditions. In the following description, color references are made to The Royal Horticultural Society Colour Chart, 2015 Edition, except where general terms of ordinary dictionary significance arc used.

Botanical classification: *Dahlia hybrida* 'BKDAOBI'.

Parentage: Naturally-occurring branch mutation of *Dahlia hybrida* 'BKDADO', disclosed in U.S. Plant Pat. No. 28,287.

Propagation:

*Type*.—By terminal cuttings.

*Time to initiate roots, summer*.—About 16 days at temperatures ranging from 18° C. to 21° C.

*Time to initiate roots, winter*.—About 19 days at temperatures ranging from 19° C. to 21° C.

*Time to produce a rooted young plant, summer*.—About 21 days at temperatures ranging from 18° C. to 21° C.

*Time to produce a rooted young plant, winter*.—About 23 days at temperatures ranging from 19° C. to 21° C.

*Root description*.—Medium in thickness, fibrous; typically white to light brown in color, actual color of the roots is dependent on substrate composition, water quality, fertilizers, substrate temperature and physiological age of roots; tuber development has not been observed on plants of the new *Dahlia*.

*Rooting habit*.—Moderately freely branching; medium density.

Plant description:

*Plant and growth habit*.—Broadly upright and mounding plant form; overall plant shape, flattened globular; freely basal branching habit with about four primary branches developing per plant; inflorescences held above the foliar plane on strong peduncles; bushy and dense growth habit; pinching is not required but will improve branching habit; moderately vigorous growth habit.

*Plant height, soil level to top of foliar plane*.—About 20.9 cm.

*Plant height, soil level to top of floral plane*.—About 32.5 cm.

*Plant diameter or spread*.—About 36.8 cm.

*Lateral branches*.—Length: About 14.9 cm. Diameter: About 6 mm. Internode length: About 3.3 cm. Aspect: Primary branches are mostly erect; secondary branches, about 40° from primary branch axis. Strength: Moderately strong. Texture and luster: Smooth, glabrous; glossy. Color, developing: Close to between 152A and N200A. Color, developed: Close to 146A tinged with close to 200D.

Leaf & leaflet description:

*Arrangement*.—Leaves opposite and compound with three or five leaflets.

*Length, leaves*.—About 16.1 cm.

*Length, terminal leaflets*.—About 10.3 cm.

*Width, leaves*.—About 17.8 cm.

*Width, terminal leaflets*.—About 5.9 cm.

*Shape, leaves in overall outline*.—Ovate.

*Shape, leaflets*.—Ovate.

*Apex, leaflets*.—Acute to apiculate.

*Base, leaflets*.—Attenuate.

*Margin, leaflets*.—Coarsely serrate.

*Venation pattern, leaflets*.—Pinnate.

*Texture and luster, upper surface, leaflets*.—Slightly rugose, sparsely pubescent; slightly velvety; slightly glossy.

*Texture and luster, lower surface, leaflets*.—Smooth, sparsely pubescent; matte.

*Color*.—Developing leaflets, upper surface: Close to between NN137A and 139A. Developing leaflets, lower surface: Close to NN137D. Fully expanded leaflets, upper surface: Slightly darker than between 147A and N189A; venation, close to 191A. Fully expanded leaflets, lower surface: Close to 143A; venation, close to 146A.

*Petioles*.—Length: About 4.9 cm. Width: About 4.5 mm. Height: About 4.5 mm. Strength: Moderately strong to strong. Texture and luster, upper and lower surfaces: Smooth, glabrous; glossy. Color, upper surface: Close to 146A to 146B. Color, lower surface: Close to 146B.

Inflorescence description:

*Appearance and arrangement*.—Double inflorescence form with ray and disc florets forming acropetally on a receptacle; inflorescences positioned above and beyond the foliar plane on strong peduncles; inflorescences face mostly upright; freely flowering habit with about 18 inflorescences developing per plant.

*Fragrance*.—Faintly fragrant; sweet, pleasant.

*Flowering response and flowering period*.—Early flowering habit, plants begin flowering about 62 days after planting; plants flower continuously during the autumn into the winter in The Netherlands.

*Post-production longevity*.—Inflorescences maintain good substance for about ten days on the plant; inflorescences persistent.

*Inflorescence buds*.—Height: About 1.1 cm. Diameter: About 1.6 cm. Shape: Flattened globular. Texture and luster: Smooth, glabrous; glossy. Color: Close to 144B to 144C; towards the apex, close to 46D.

*Inflorescence size*.—Diameter: About 9.6 cm. Depth (height): About 7.9 cm. Disc diameter: About 1.6 cm.

*Receptacles*.—Height: About 3 mm. Diameter: About 6 mm. Shape: Flattened globular. Color: Close to 145C.

*Ray florets*.—Quantity per inflorescence and arrangement: About 100 arranged in about six whorls. Length: About 4.1 cm. Width: About 2.2 cm. Shape: Broadly obovate. Apex: Obtuse to shallowly retuse. Base: Attenuate. Margin: Entire. Aspect: Upright to roughly horizontal and eventually downward, moderately to strongly concave. Texture and luster, upper and lower surfaces: Smooth, glabrous; moderately velvety; matte. Color: When opening, upper surface; Close to 26A and towards the base, close to 1A. When opening, lower surface: Close to N45A and towards the base, close to 53A. Fully opened, upper surface: Close to 26B and towards the base, close to 6C; venation, same as lamina, close to 26B and towards the base, close to 6C; colors do not change with development. Fully opened, lower surface: Close to 42A and towards the base, close to 42C;

venation, close to 50B and towards the base, close to 11D; with development, colors become closer to 53C and towards the base, close to 42B to 42C.

*Disc florets*.—Quantity per inflorescence and arrangement: About 25 massed at the center of the inflorescence in about three spiral whorls. Length: About 1.4 cm. Diameter: About 4 mm. Shape: Tubular, elongated; apices, acute. Texture and luster, inner and outer surfaces: Smooth, glabrous; glossy. Color, when opening, inner and outer surfaces: Apex: Close to 14B. Mid-section and base: Close to 151C. Color, fully opened, inner and outer surfaces: Apex: Close to 14B. Mid-section and base: Close to 151C.

*Phyllaries*.—Quantity per inflorescence and arrangement: About eight arranged in about two whorls. Length: About 1.3 cm. Width: About 7 mm. Shape: Ovate. Apex: Acute. Base: Cuneate. Margin: Entire. Texture and luster, upper and lower surfaces: Smooth, glabrous; moderately glossy. Color, upper surface: Close to NN137A. Color, lower surface: Close to NN137B.

*Peduncles*.—Length, terminal peduncle: About 17.2 cm. Diameter, terminal peduncle: About 3.5 mm. Strength: Strong. Texture and luster: Smooth, glabrous; moderately glossy. Color: Close to 144A; proximally, tinged with close to N199A.

*Reproductive organs*.—Androecium, present on disc florets only: Quantity per floret: About four. Filament length: About 1 mm. Filament color: Close to 151D. Anther shape: Narrowly oblong. Anther length: About 4 mm. Anther color: Close to 13A. Pollen amount: Abundant. Pollen color: Close to N25C. Gynoecium, present on disc florets only: Quantity per floret: One. Pistil length: About 1.2 cm. Style length: About 8 mm. Style color: Close to 151D. Stigma diameter: About 4 mm. Stigma shape: Cleft, decurrent. Stigma color: Close to 17A to 17B. Ovary color: Close to 145D. Seeds and fruits: Seed and fruit development have not been observed on plants of the new *Dahlia*.

Disease & pest resistance: Plants of the new *Dahlia* have not been observed to be resistant to pathogens and pests common to *Dahlia* plants.

Temperature tolerance: Plants of the new *Dahlia* have been observed to tolerate high temperatures of about 30° C. and to be suitable for USDA Hardiness Zones 9 to 11.

It is claimed:

1. A new and distinct *Dahlia* plant named 'BKDAOBI' as illustrated and described.

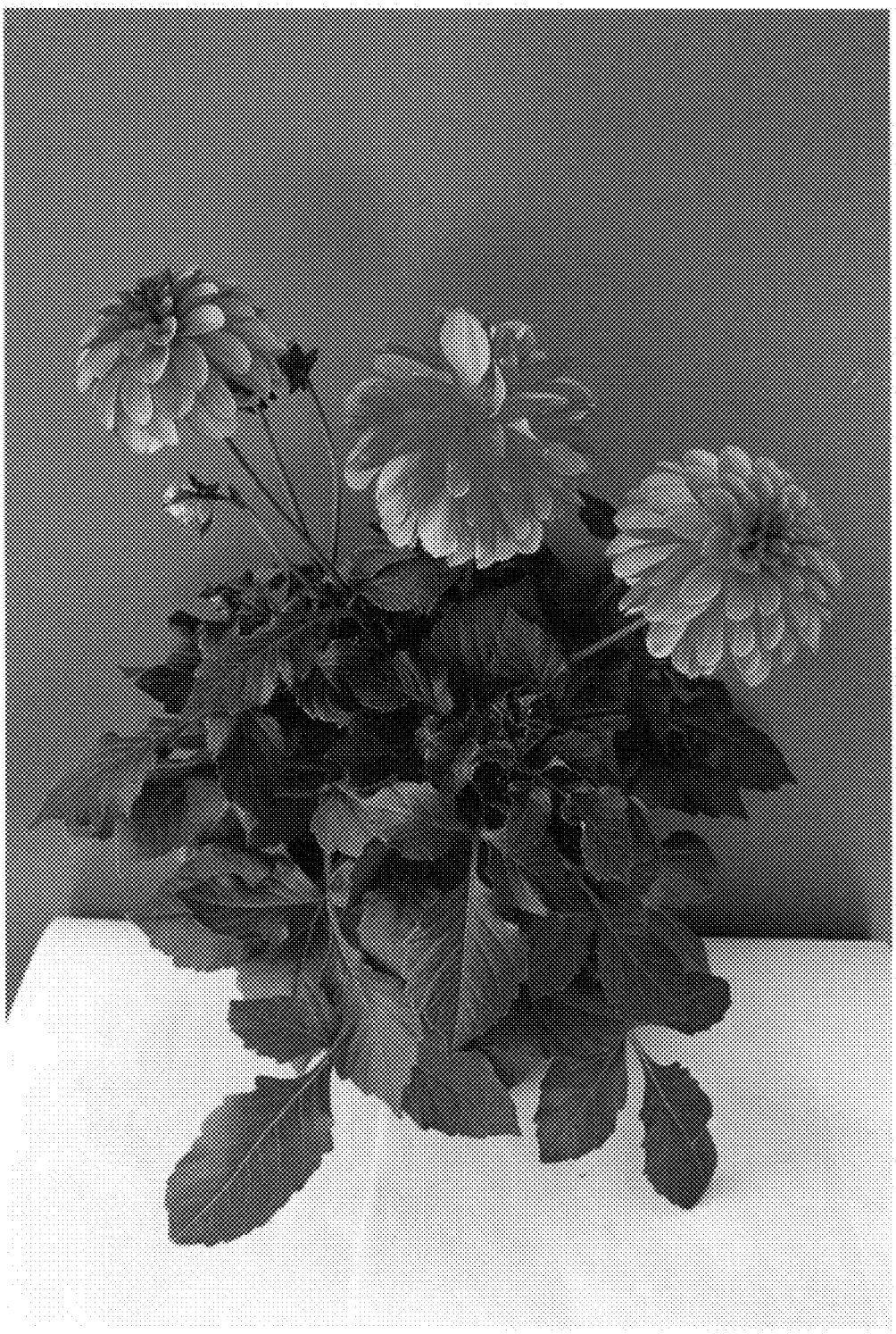

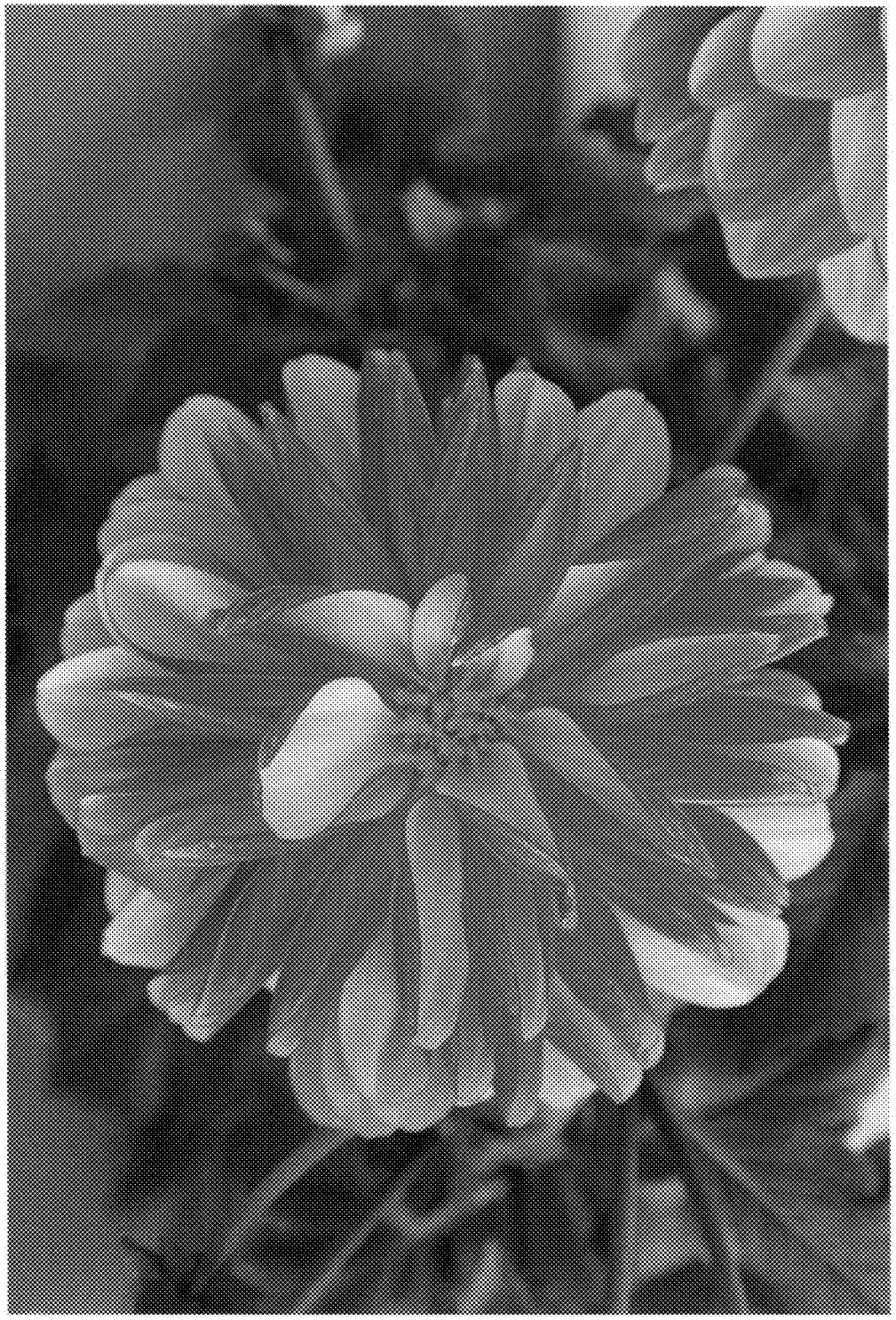

* * * * *